United States Patent [19]

De Graff

[11] Patent Number: 4,695,665
[45] Date of Patent: Sep. 22, 1987

[54] PROCESS FOR ALKYLATION OF HYDROCARBONS

[75] Inventor: Richard R. De Graff, Deerfield, Ill.

[73] Assignee: UOP Inc., Des Plaines, Ill.

[21] Appl. No.: 881,536

[22] Filed: Jul. 2, 1986

[51] Int. Cl.$^4$ .......................... C07C 3/54; C07C 7/04
[52] U.S. Cl. .................................... 585/450; 585/466; 203/78; 203/82
[58] Field of Search .............. 585/450, 451, 466, 467; 203/42, 78, 82, 98; 208/340, 350-355, 358, 368

[56] References Cited

U.S. PATENT DOCUMENTS

| | | | |
|---|---|---|---|
| 2,281,282 | 4/1942 | Gerhold | 208/350 |
| 3,371,032 | 2/1968 | Witt et al. | 203/98 X |
| 3,383,308 | 5/1968 | Wickham et al. | 203/98 X |
| 3,437,708 | 4/1969 | Gantt | 585/450 |
| 3,499,826 | 3/1970 | Sulzbach et al. | 585/450 X |
| 3,510,534 | 5/1970 | Sulzbach | 260/671 |
| 3,518,165 | 6/1970 | Ward | 203/78 |
| 3,520,944 | 7/1970 | Ward | 260/671 |
| 3,520,945 | 7/1970 | DeGraff | 260/671 |
| 3,527,823 | 9/1970 | Jones | 260/671 |
| 3,950,448 | 4/1976 | Witt | 585/450 |
| 4,051,191 | 9/1977 | Ward | 260/671 R |
| 4,108,914 | 8/1978 | Gewartowski | 585/450 X |
| 4,410,400 | 10/1983 | Preusser et al. | 203/98 X |
| 4,555,311 | 11/1985 | Ward | 203/98 X |

Primary Examiner—Andrew H. Metz
Assistant Examiner—Glenn Caldarola
Attorney, Agent, or Firm—Thomas K. McBride; John F. Spears, Jr.

[57] ABSTRACT

A process flow is presented for a hydrocarbon conversion process in which a relatively volatile hydrocarbon is separated from less volatile feed and product hydrocarbons present in a reaction zone effluent stream. The preferred usage is in the alkylation of benzene with propylene. The reaction zone effluent stream is passed into a lower portion of a rectified separation zone. Recycle aromatic hydrocarbon is passed into a contact exchanger/absorber present in the top portion of the rectified separation zone. The liquid collected at the bottom of the contact exchanger is removed as a sidecut stream and passed into the reaction zone.

14 Claims, 1 Drawing Figure

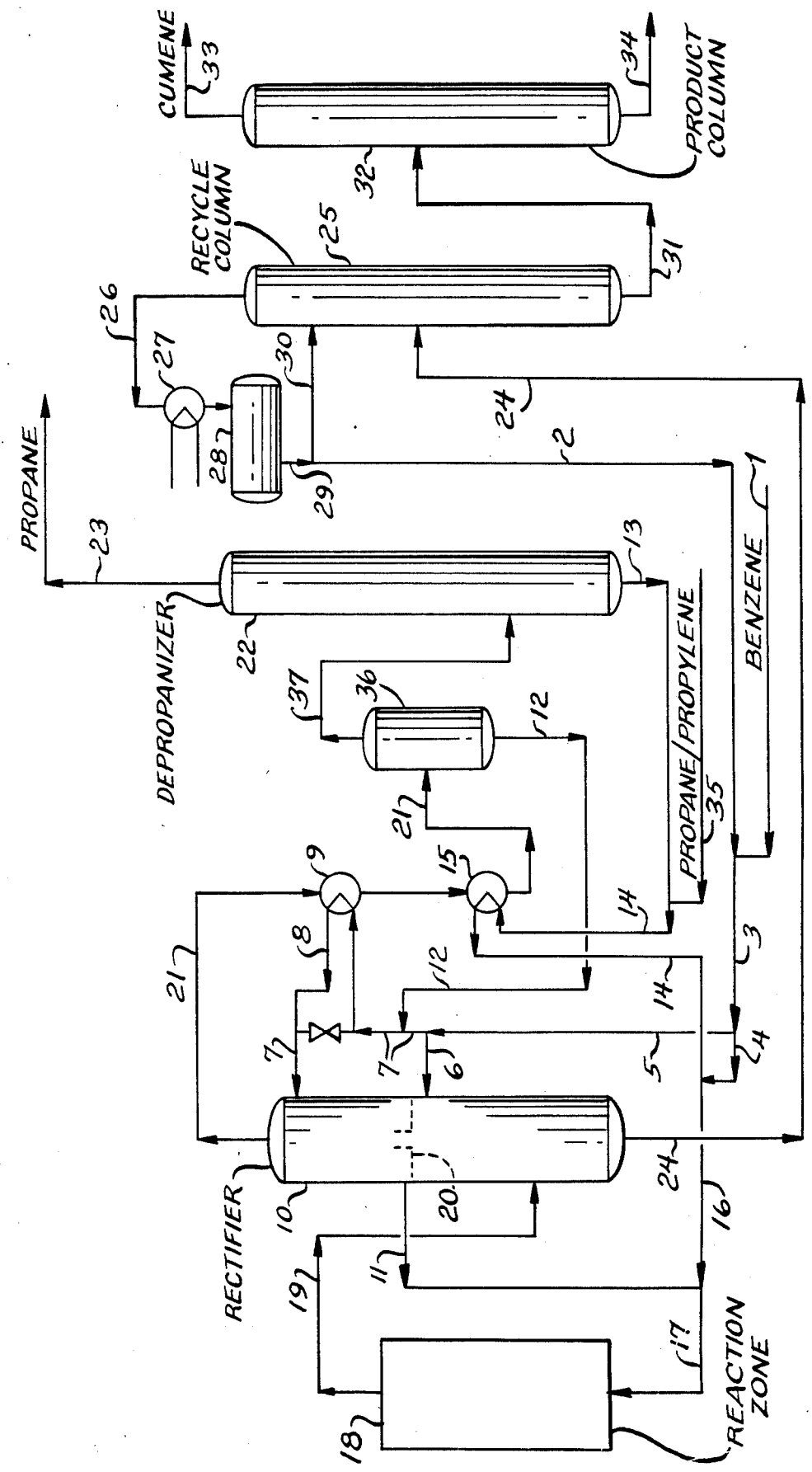

PROCESS FOR ALKYLATION OF HYDROCARBONS

FIELD OF THE INVENTION

The invention relates to the hydrocarbon conversion process commonly referred to as catalytic condensation in which a light olefinic hydrocarbon is consumed in the production of heavier hydrocarbons. The invention more directly relates to a process in which the catalytic condensation or alkylation of benzene with propylene contained in a mixed propane-propylene feedstream is performed to produce alkylaromatic hydrocarbons. The invention is specifically concerned with providing an improved method of separating the light hydrocarbons present in the reaction zone effluent from the less volatile components of the effluent stream and for increasing the recovery of heat from the reaction zone effluent stream.

INFORMATION DISCLOSURE

The catalytic condensation of light olefins is an established commercial process used to produce gasoline blending components. It is also widely utilized in the production of alkyl aromatic hydrocarbons by the reaction of a light olefinic feed hydrocarbon with an aromatic feed hydrocarbon. U.S. Pat. No. 3,527,823 issued to E. K. Jones illustrates a straightforward process flow for the production of cumene by the reaction of benzene and propylene. The propylene containing feedstream, the benzene feedstream and recycle benzene from the overhead of the benzene recycle column are passed into a reaction zone. The reaction zone effluent stream is passed into a depropanizer column. Propane is recovered as the overhead product of this column and the bottoms stream of the depropanizer column is passed into the benzene recycle column. The bottoms stream of the benzene recycle column is passed into a cumene rerun column, with a cumene rich product being recovered as the net overhead product of this column.

A number of different separation methods have been developed to handle the effluent stream of a catalytic condensation unit used to produce cumene. Several of these methods pass the entire cumene reactor effluent into a rectified flash vessel or separation zone. These various process flows are believed exemplified by U.S. Pat. No. 3,510,534 issued to T. L. Sulzbach, U.S. Pat. Nos. 3,518,165 and 3,520,944 issued to D. J. Ward and U.S. Pat. No. 3,520,945 issued to the applicant herein. These references illustrate the various configurations possible in the separation steps downstream of this first stage rectification zone.

U.S. Pat. No. 4,051,191 issued to D. J. Ward illustrates another process flow for the alkylation of aromatic hydrocarbons in which the effluent stream is passed into a rectified separation column. This reference illustrates the passage of a portion of the recycle benzene stream removed from the overhead of the recycle column into the top of the rectifying vessel which receives the reactor effluent.

The subject process employs a direct contact heat exchanger. In such a device two fluid streams of different phases are brought into direct contact for the purpose of exchanging heat between the two streams. Typically, this contacting involves the countercurrent passage of a descending liquid stream and a rising vapor stream, with the contacting being promoted through the use of various contact materials such as trays or the packing material resembling that employed in fractionation columns. U.S. Pat. No. 3,950,448 issued to P. A. Witt describes the use of a contact heat exchanger-condenser in the upper portion of a stripping column which receives the effluent stream of an alkylation reactor. Similar equipment is employed in the other columns of the process, with this arrangement having been chosen to reduce the pressure drop through the column and increase the overall efficiency of the process.

BRIEF SUMMARY OF THE INVENTION

The invention is an improved catalytic condensation process. In the subject process, the effluent stream of the catalytic condensation reaction zone is charged to a two-part rectified separation zone. The lower portion of this zone, referred to herein as the rectification zone, receives a portion of the recycle feed hydrocarbon as reflux material. The upper portion of the rectified separation zone receives an additional portion of the recycle feed hydrocarbon stream. The upper zone is referred to herein as the contact-exchanging zone. A liquid phase stream is withdrawn at the bottom of the contact-exchanging zone, with this liquid phase side stream being passed into the reaction zone. This manner of operation provides a highly effective separation of propane or other light hydrocarbons from the remaining less volatile feed and product hydrocarbons. This method of operation also improves the heat recovery from the overhead stream of the rectified separation zone and thereby increases the overall thermal efficiency of the process.

A broad embodiment of the invention may be characterized as a hydrocarbon conversion process which comprises the steps of passing a reaction zone effluent stream comprising a volatile light hydrocarbon and less volatile feed and product hydrocarbons into a lower portion of a rectified separation zone operated at conditions effective to separate the entering hydrocarbons into an overhead vapor stream which is rich in the light hydrocarbon and a bottoms stream comprising the feed and product hydrocarbons; separating the bottoms stream in a fractionation zone into a liquid-phase recycle stream which is rich in the feed hydrocarbon and a product stream which is rich in the product hydrocarbon, and withdrawing the product stream from the process; passing a portion of the recycle stream into a contact exchanger located in an upper portion of the rectified separation zone and which receives a rectified vapor stream comprising the volatile light hydrocarbon and the feed hydrocarbon from the lower portion of the rectified separation zone, removing heat and the feed hydrocarbon from the rectifier vapor stream by direct contact and producing said overhead vapor stream and a rectifier exchanger liquid stream which is withdrawn from the rectified separation zone at a point above the lower portion of the rectified separation zone and below the contact exchanger; and, passing the rectifier exchanger liquid stream and a feed stream comprising the volatile light hydrocarbon into a reaction zone maintained at reaction conditions and producing the reaction zone effluent stream.

BRIEF DESCRIPTION OF THE DRAWING

The Drawing is a simplified process flow diagram illustrating the passage of the reaction zone effluent stream into the rectifier 10. Recycle benzene from the overhead of column 25 is passed into the top of both the upper and lower zones of the rectifier 10 with a liquid phase stream comprising the recycled benzene and any condensed or adsorbed hydrocarbons being removed in line 11 for recycling to the reaction zone.

DETAILED DESCRIPTION

Catalytic condensation processes are useful in converting light aliphatic olefins such as propylene or butylene into higher molecular weight hydrocarbons of greater economic value. There are two basic types of catalytic condensation processes. These two types of processes are distinguished by their product and feedstreams. A first type of catalytic condensation process may be considered as a form of an oligomerization process and may be used to convert propylene into trimer or tetramer which may then be used to manufacture detergents. This particular form of the cataltyic condensation process is often utilized to produce good quality gasoline blending components from propylene or butylene. The subject process may be applied to this form of the catalytic condensation process with the product hydrocarbons being $C_8+$ olefinic hydrocarbons. However, the subject process is preferably applied to a second form the the catalytic condensation process in which the propylene or butylene is reacted with an aromatic feed hydrocarbon to produce alkyl aromatic hydrocarbons. As this is the preferred form of the invention, the following description will be cast mainly in terms of the production of cumene. Those skilled in the art will readily recognize that the various product hydrocarbons of an oligomerization process may be substituted for the aromatic hydrocarbon described herein in adapting the subject invention to the production of $C_8$ or $C_9+$ olefinic hydrocarbons.

The economical operation of any petrochemical or petroleum refining process is very sensitive to the amount of fuel which is consumed within the process for such purposes as heating reaction zone feed streams to the required reaction zone inlet temperature. It is an objective of the subect invention to increase the overall efficiency of a catalytic condensation process. It is a specific objective of the subject invention to increase the amount of heat recovered from the effluent stream of a catalytic condensation. A further specific objective of the subject invention is a reduction in the amount of heat which must be added to the feedstream to the catalytic reaction zone and thereby a reduction in the utility cost of operating the process.

In the subject process these objectives are achieved by passing a vaporous portion of the reaction zone effluent stream upward through a contact-exchanging or contact-condensing zone located in the upper portion of a rectified separation zone. At the same time recycled benzene is passed downward through this same contact zone to recover heat present in these vapors. This method of operation allows a much closer "approach" between the temperature of the benzene liquid-containing stream being removed from the zone and the vapors entering the zone. That is, the temperature difference between these two streams is less than that which would be achieved through the utilization of a conventional indirect heat exchange means.

The production of alkylaromatic hydrocarbons in the subject process requires that two separate feedstreams are passed into the process. A first feedstream must provide the light (low carbon number) acyclic olefinic hydrocarbon which is consumed in the process. The feed olefinic hydrocarbon is preferably propylene, but could be one or more of the butylenes or even a mixture of propylene and butylenes. $C_5$ olefins could also be charged to the subject process. Preferably, this feedstream is a rather pure stream which contains very little (less than 5 mole percent) of any hydrocarbons having other than 3 or 4 carbon atoms per molecule. Any hydrocarbons other than propane or propylene preferably have more than 3 carbon atoms per molecule. It is highly preferred that the feedstream contains over 90 percent hydrocarbons having a single number of carbon atoms per molecule. As very high-purity streams of olefinic hydrocarbons are not normally produced and would normally require expensive separation procedures, the feedstream to the subject process would typically comprise an admixture of a light olefinic hydrocarbon and a light paraffinic hydrocarbon having the same number of carbon atoms per molecule. It is especially preferred that the feedstream contains between about 30 to about 99 mole percent of the light olefinic feed hydrocarbon. The following description of the inventive concept is cast mainly in terms of consuming the preferred propylene feed but also applies to mixed propylene-butylene or high-purity butylene feedstreams.

The second hydrocarbon feedstream to the subject process preferably comprises a monocyclic aromatic hydrocarbon although polycyclic aromatic hydrocarbons may also be alkylated using the subject process. These aromatic hydrocarbons include benzene, toluene, the xylenes, ethylbenzene, normal propylbenzene, isopropylbenzene and other cyclic compounds. The preferred feed aromatic hydrocarbon is benzene, with recent developments indicating the alkylation of toluene will also have significant commercial importance in the future. Typical products are cumene and cymene (isopropyltoluene).

The operational steps of the subject process are illustrated in the Drawing. The Drawing illustrates a slightly modified version of the preferred embodiment of the invention. The flash drum 36 is depicted only because of its presence in the commercial process unit which was used as the basis of the example. The example below is based upon the flows resulting from a revamp to this unit, and the flash drum is believed necessary to clearly present the example. It can otherwise be eliminated as it is not necessary to the practice of the invention. This presentation of one embodiment of the invention is not intended to preclude from the scope of the invention those other embodiments set out herein or which result from the normal and expected modification of those embodiments. The Drawing has been simplified by representing only those pieces of process equipment which are believed necessary for a complete understanding of the subject invention. Therefore, various other pieces of process equipment such as pumps, process control systems, valves, and vessel internals, etc. have not been illustrated. These normal process accouterments may be similar to those now used in the art and which are familiar to those skilled in the art of process design and construction.

Referring now to the Drawing, a first feedstream, which is a high-purity stream of benzene, enters the process through line 1. This feedstream is admixed with recycle benzene flowing through line 2 and is then transported through line 3 to the junction with lines 4 and 5. There is normally no flow through line 4 and the entire recycle and feed benzene stream flows through line 5. A second feed stream, which comprises propylene and propane, enters the process via line 35 and is admixed with recycled propane and benzene from line 13. Line 14 supplies the recycled propane and feed propylene to the juncture with line 11. A liquid phase stream comprising benzene and some propane carried by line 11 is admixed into these hydrocarbons and the resultant admixture is passed through line 17 into the reaction zone 18.

Within the reaction zone, the entering reactants are contacted with a suitable catalyst maintained at catalytic condensation conditions with the result that a significant quantity of the originally charged propylene is reacted with benzene to produce cumene. There is thereby produced a reaction zone effluent stream carried by line 19 which comprises propane, benzene and cumene.

This reaction zone effluent stream is passed into a lower portion of the rectifier 10 preferably at a vertical elevation below the vapor-liquid contacting trays or packing present within the uppermost region of the rectification zone. The rectification zone comprises that portion of the rectifier 10 located below the liquid trapout tray 20. The trapout tray 20 represents any of a number of mechanical contrivances which could be placed at an intermediate vertical elevation within the rectifier 10 and which functions to prevent the downward passage of liquid phase hydrocarbons at this point within the rectifier while still allowing vapor to pass freely upward into the contact-exchanging zone which is located above the trapout 20. The upwardly rising vapors are countercurrently contacted with a stream of benzene-rich liquid fed to an upper section of the contacting exchanging zone through line 7. This countercurrent contacting effects the removal of the heavier aromatic hydrocarbons from the upwardly rising vapors. The actual removal may be caused by several different phenomena including condensation and absorption into the descending liquid.

An overhead vapor stream of line 21 is removed from the top of the rectified separation zone. This vapor stream will comprise propane and a sizeable amount of benzene but only a very relatively minor amount of cumene. The vaporous overhead stream of the rectified separation zone is cooled in the indirect heat exchange means 9 and 15. This cooling will cause the condensation of benzene such that the material entering the optional flash drum 36 through line 21 will be a mixed-phase stream. The condensate collected in the flash drum is rich in benzene and is returned to the rectifier 10 via lines 12 and 7. Those skilled in the art will recognize that it will often be more desirable to admix the contents of line 12 into the line 7 at a point downstream of the heat exchanger 9. The vapor from the flash drum is passed through a cooler not shown and then into a depropanizer 22 via line 37. The depropanizer column 22 is designed and operated to reject excess propane as a net overhead stream removed through line 23. The propane will normally be withdrawn as a net liquid stream from an overhead receiver not shown.

Essentially all of the $C_6+$ hydrocarbons, basically benzene, which enter the depropanizer column 22 are concentrated into a net bottoms stream removed from the column through line 13. The amount of propane allowed to remain in the bottoms stream is adjusted depending on the propylene concentration of the second feed stream in order to achieve the desired propane to propylene ratio in the total reactor charge material. This separation is promoted through the use of a reboiler means not shown which is present at the bottom of the depropanizer column. The liquid phase bottoms stream of the depropanizer column is admixed with the propane/propylene feedstream of line 35 and passed into line 14. This admixture of propane, propylene and benzene is then heated in the indirect heat exchange means 15 prior to being passed into the reaction zone via lines 14, 16 and 17.

A bottoms liquid stream is removed from the rectifier 10 in line 24. This liquid stream should comprise a sizeable quantity of benzene and all of the cumene produced within the reaction zone. This liquid phase stream is transferred into a midpoint of the reboiled recycle column 25. This column is designed and operated to concentrate the desired recycle component or components into an overhead product stream and to simultaneously concentrate the desired product of the process into a net bottoms stream. Accordingly, an overhead vapor stream which is rich in benzene is removed from the top of the column in line 26 and condensed in the indirect heat exchanger 27. The condensate is collected in the overhead receiver 28 and withdrawn through line 29. A first portion of the condensate is returned to the recycle column 25 as reflux through line 30, with the remaining portion of the condensate flowing through line 2. The liquid flowing through line 2 is the primary recycle benzene stream of the subject process. In other embodiments of the process, this stream could be rich in different feed hydrocarbons, such as toluene, or $C_6$, $C_7$, or $C_8$ hydrocarbons produced in the reaction zone by an oligomerization reaction.

As previously described, the feed benzene stream of line 1 is admixed with the recycle benzene of line 2. All of this admixture of the feed and recycle benzene is normally diverted through line 5 for passage into the rectifier 10. A first portion of the benzene stream of line 5 is passed into the top of the rectification zone through line 6 at a point above the contacting material present in the rectification zone. The remaining portion of the benzene flowing through line 5 enters line 7. A portion of the benzene of line 7 is preferably diverted into line 8 for heating by indirect heat exchange against the overhead stream of the rectifier in the exchanger 9. The benzene stream of line 8 is then reunited with the unheated benzene and passed into the rectifier 10 at the top of the contact-exchanging zone. Some of the benzene which enters the rectifier through line 6 will be vaporized and will pass upward into the contact-exchanging zone through the vapor passageway provided in the liquid trapout means 20. The remaining portion of the benzene of line 6 will descend through the column and will be removed with the liquid of line 24. A major portion of the benzene of line 7 will descend through the contact-exchanging zone and be removed through line 11 in the liquid-phase side stream. A portion of the benzene from line 7 will however be vaporized and leave the rectifier 10 through line 21.

The net bottoms stream of the benzene or recycle column 25 is passed through line 31 into an intermediate point of a product fractionation column 32. The product column is often referred to as the cumene column. This column will preferably have an overhead condensing system and a reboiling system not shown. The column is designed and operated to separate the entering hydrocarbons into a net overhead product stream rich in cumene or other product hydrocarbon withdrawn through line 33 and a net bottoms product stream comprising heavy by-products of the catalytic condensation reaction and which is withdrawn through line 34.

It is readily apparent that the process flow shown in the Drawing can be modified in several ways without departing from the concept of the invention. For instance, both the benzene feedstream of line 1 and the propylenecontaining feedstream of line 35 can be passed into the process at a wide variety of places. For instance, the benzene stream could be admixed into the material flowing through line 17. The propane/propylene stream of line 35 could be admixed with the stream of line 11 or passed directly into the reaction zone for admixture therein with the entering benzene.

The differing temperatures of the various process streams allow the application of a significant number of heat exchange variations which are not illustrated in the Drawing for the sake of simplicity. For instance, there is no showing in the Drawing of any attempt to recover heat present in the overhead vapor stream of the fractionation columns and there is no heat exchange shown on the feed streams or the effluent of the reaction zone other than that involved in the subject invention. It is also apparent to those skilled in the art that significant variation can be achieved in the design of the reaction zone and the vessel internals of the various fractionation columns and the rectifier 10. The entire configuration of the product recovery fractionation zone could also be revised or different product recovery techiques could be employed. For instance, it may be advisable in certain instances or with technology developed in the future to employ an adsorptive separation or extractive distillation to recover the product or products of the process.

Further variation in the overall flow of the process employing the subject invention may be due to the specific type of catalyst employed within the reaction zone. For instance, it is known that the passage of aromatic hydrocarbons through an alkylation zone tends to leach chemically combined water out of the preferred SPA catalyst described below. This is acknowledged in U.S. Pat. Nos. 3,510,534 and 3,520,945, the latter of which is directed to the control of the state of hydration of the catalyst. The 15 water content of the catalyst is important since dehydration causes the SPA catalyst to deteriorate by powdering and caking, while excess water causes the catalyst to soften and eventually form a sludge which will plug the reactor. Water is therefore injected into the feedstream to maintain the catalyst at the proper state of hydration by replacing the water leached from the catalyst. The rate of this rejection is used to control the catalyst hydration level, and the feedstreams are therefore maintained as dry as practical prior to the water injection point. This results in the total amount of water contained in the feed being essentially equal to the amount of water injected. Typical water injection rates are from about 100 ppm to 2,000 ppm in the reaction of aromatic hydrocarbons with light olefins. A preferred water addition rate during the production of cumene is from about 200 to 300 ppm of the combined feed to the reaction zone. Also not shown on the Drawing is a flash separation vessel such as that described in previously referred to U.S. Pat. No. 4,051,191, which is useful in removing acid from the liquid-phase effluent stream of the rectifier. The use of this flash vessel is preferred to limit the amount of acid passed into the recycle column 25. Another common feature not illustrated in the Drawing is the removal of a drag benzene stream. This stream is typically removed from the recycle benzene stream and serves to limit the accumulation within the process of various hydrocarbons which due to the boiling points would tend to accumulate within the benzene recycle stream.

The rectifier or rectified flash separation zone 10 is preferably a trayed column containing vapor-liquid contacting trays both above and below the liquid trapout and withdrawal means 20. Alternatively, this vessel could contain a packing type of contact material above and/or below the trapout liquid withdrawal tray. Preferably, no reboiling means is provided at the bottom of this rectifier, with the relative amounts of vapor and liquid withdrawal being governed by the composition of the incoming reaction zone effluent stream and the temperature and amounts of the benzene charged to the rectifying zone via lines 6 and 7. The liquid which accumulates in the bottom of the rectifier 10 is withdrawn on the basis of level control.

The catalytic condensation process may be performed using several different types of catalyst within the reaction zone. For instance, U.S. Pat. Nos. 3,932,553 and 3,997,621 describe processes in which boron trifluoride is utilized as a catalyst. Both of these catalytic systems utilize a minor amount of an additive to control the extent to which the reaction proceeds. In both of these references, the catalyst system appears to be homogeneous. Other homogeneous catalyst systems comprising $BF_3$ and a promoter are described in U.S. Pat. Nos. 4,434,308; 4,413,156 and 4,395,578. Friedel-Crafts catalysts in general are often effective at dimerization. Aluminum trichloride ($AlCl_3$) promoted with a small amount of water or other hydroxy compound can be employed. Promoters or catalyst components can be recycled as vapor drawn off vessel 36 or the overhead receiver of column 22 or condensed into the recycle stream of line 12.

It is highly preferred that a heterogeneous catalyst system is employed. Heterogeneous catalytic systems for the production of higher molecular weight olefins by the oligomerization or dimerization of light olefins are described in U.S. Pat. Nos. 3,906,053; 3,916,019; 3,959,400; 3,981,940; 3,981,941; 4,365,105; 4,394,296; and 4,476,342. U.S. Pat. No. 4,400,565 describes a patent system comprising a cationic ion exchange resin and added boron trifluoride. As may be expected from the large number of processes, the conditions employed within the reaction zone may vary widely. For instance, the just cited references specify that the reaction may be performed at temperatures ranging from −50 degrees to 250 degrees Celsius and at a pressure ranging from about 1.3 to approximately 100 atmospheres gauge.

A widely used catalyst is the SPA (solid phosphoric acid) type catalyst. As used herein, the term "SPA catalyst" is intended to indicate a solid catalyst which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are however possible. Further details as to the composition, production, and use of SPA catalysts may be obtained from U.S. Pat. Nos. 3,050,472; 3,050,473; 3,132,109 and 4,334,118 from other references. Any of the above mentioned catalyst systems, and also those which are yet to be developed, may be employed in the subject process.

The catalyst is preferably disposed in fixed beds in the chamber-type reactor structure. The temperature of the reactants is preferably also controlled by recycling inert hydrocarbons (propane) which act as a heat sink. The catalyst beds are preferably contained within a number of cylindrical, vertically oriented vessels. Separate parallel or series reactors may be used in large process units. The reaction zone may be maintained at widely varying conditions due to the previously listed variables including the use of different catalysts. A broad range of suitable pressures is from about 105 to 8400 kPag, with a preferred pressure range for an SPA catalyst being from 3000 to 8500 kPag. The pressure is preferably at least sufficiently high to maintain some liquid phase hydrocarbons within the reaction zone. The temperature maintained in this zone with the preferred SPA catalyst may vary from about 120 to about 260 degrees Celsius with a temperature over 150 degrees Celsius being preferred. Steam or water may be fed into the reactor to maintain the desired water content in the preferred catalyst.

The following example is presented to further illustrate the invention. This example is based upon detailed engineering calculations and the results and experience acquired in the operation of prior art catalytic condensation units. The flow of the process is as in the Drawing. The benzene feedstream has a flow rate of about 600 moles per hour. The 902 mole per hour olefin feedstream contains 590 moles per hour of propylene and about 305 moles per hour of propane. The total combined feedstream to the reaction zone including injected water has a flow rate of approximately 6,211 moles per hour and is divided between four upflow fixed bed reactors containing the preferred SPA catalyst and operated as set out herein. The total reaction zone effluent stream is a mixed-phase stream having a flow rate of about 5,626 moles per hour. This stream contains about 609 moles per hour of cumene, 3,495 moles per hour of benzene and 1,129 moles per hour of propane. It contains essentially no propylene. The remainder of this stream comprises an admixture of a large number of $C_4$ to $C_{12}$ hydrocarbons and a small amount of water.

The total reaction zone effluent stream is passed through a pressure reduction valve and into the rectified separation zone at a temperature of 217 degrees Celsius. The separation zone is divided by a liquid collection or trapout tray into an upper contact-exchanging zone containing nine vapor-liquid contacting trays and lower rectification section containing fifteen vapor-liquid contacting trays. The rectified separation zone has a 2.75 meter internal diameter in the trayed sections of the vessel. The separation zone is operated at a pressure of about 1890 kPag (274 psig). The overhead vapor stream removed from the top of the rectified separation zone has a flow rate of about 3,495 moles per hour, of which approximately 2,002 moles per hour is benzene and 1,281 moles per hour is propane. The overhead vapor stream has a temperature of 184 degrees Celsius. A liquid stream comprising recycle benzene and flash drum liquid having a flow rate of about 3,364 moles per hour and a temperature of approximately 149 degrees Celsius is passed into the top of the contact-heat exchange zone of the rectified separation zone. This liquid stream contains about 1,322 moles per hour of recycle benzene from the recycle column. A liquid sidestream is withdrawn at the trapout means with a temperature of 196 degrees Celsius and a flow rate of about 4,159 moles per hour. This stream is passed into the reaction zone. A stream of recycle benzene having a flow rate of about 1,100 moles per hour and a temperature of approximately 66 degrees Celsius is passed into the top of the rectification zone of the rectified separation vessel. A rectified separation zone bottoms stream is removed at the rate of about 2,430 moles per hour. This stream comprises approximately 1,595 moles per hour of benzene, 89 moles per hour of propane and 563 moles per hour of cumene. It has a temperature of about 216 degrees Celsius. The overhead vapor stream is cooled to about 149 degrees Celsius and is passed into the optional flash drum. The flash drum is operated at a pressure of approximately 1,813 kPag. The vapor removed from the top of the flash drum is passed into the depropanizer column. The bottoms liquid or condensate stream removed from the flash drum has a flow rate of about 2,042 moles per hour, of which about 1,540 moles per hour is benzene and about 342 moles per hour is propane. This stream is combined with recycle benzene and passed into the contact-exchanger zone. The material fed to the depropanizer column is separated into a net overhead stream having a flow rate of about 308 moles per hour, which is over 99 mole percent propane, and a net bottoms stream having a flow rate of about 1,147 moles per hour. The depropanizer bottoms stream contains about 632 moles per hour of propane, with the rest of this stream mainly comprising benzene. The rectified separation zone bottoms stream is passed into the recycle column and separated into the recycle benzene stream and a bottoms stream passed into the cumene column. The recycle benzene is divided between the upper and lower portions of the rectified separation zone.

I claim as my invention:

1. A fixed-bed hydrocarbon alkylation process which comprises the steps of:
   (a) passing a reaction zone effluent stream comprising a volatile light hydrocarbon and less volatile feed and product hydrocarbons into a lower portion of a rectified separation zone operated at conditions effective to separate the entering hydrocarbons into an overhead vapor stream which is rich in the light hydrocarbon and a bottoms stream comprising the feed and product hydrocarbons;
   (b) separating the bottoms stream in a fractionation zone into a liquid-phase recycle stream which is rich in the feed hydrocarbon and a product stream which is rich in the product hydrocarbon, and withdrawing the product stream from the process;
   (c) passing a portion of the recycle stream into a contact-exchanger located in an upper portion of the rectified separation zone and which receives a rectified vapor stream comprising the volatile light hydrocarbon and the feed hydrocarbon from the lower portion of the rectified separation zone, removing heat and the feed hydrocarbon from the rectifier vapor stream by direct contact and producing said overhead vapor stream and a rectifier exchanger liquid stream which is withdrawn from the rectified separation zone at a point above the lower portion of the rectified separation zone and below the contact-exchanger; and, (d) passing the rectifier exchanger liquid stream and a feed stream comprising the volatile light hydrocarbon into a reaction zone maintained at reaction conditions and producing the reaction zone effluent stream.

2. The process of claim 1 further characterized in that a portion of the recycle stream liquid passed into the contact-exchanger is heated by indirect heat exchange against the overhead vapor stream.

3. The process of claim 1 further characterized in that another portion of the recycle stream is passed into the lower portion of the rectified separation zone.

4. The process of claim 3 further characterized in that essentially no liquid flows downward within the rectified separation zone from the contact exchanger into the lower portion of the rectified separation zone.

5. The process of claim 3 further characterized in that the volatile light hydrocarbon is an aliphatic hydrocarbon and the feed and product hydrocarbons are aromatic hydrocarbons.

6. The process of claim 5 further characterized in that the reaction zone contains a bed of zeolitic alkylation catalyst.

7. The process of claim 5 further characterized in that the reaction zone contains a bed of SPA type catalyst.

8. A process for the production of alkylaromatic hydrocarbons which comprises the steps of:

(a) reacting a feed aromatic hydrocarbon and a feed olefinic hydrocarbon in a catalytic reaction zone and producing a reaction zone effluent stream comprising a volatile light hydrocarbon, the feed aromatic hydrocarbon and a product aromatic hydrocarbon;

(b) passing the reaction zone effluent stream into a rectified separation zone comprising a lower rectification zone and an upper contact-exchanging zone and operated at conditions effective to separate entering hydrocarbons into an overhead vapor stream which is rich in the volatile light hydrocarbon, a liquid-phase bottoms stream comprising the feed and product aromatic hydrocarbons and a liquid-phase sidestream withdrawn between the rectification zone and the contact-exchanging zone and which comprises the feed aromatic hydrocarbon;

(c) passing the sidestream into the reaction zone;

(d) separating the bottoms stream in a fractionation zone into a product stream which is rich in the product aromatic hydrocarbon and a recycle stream which is rich in the feed aromatic hydrocarbon, and withdrawing the product stream from the process; and, (e) passing at least a first portion of the recycle stream into the contact-exchanging zone of the rectified separation zone, with the recycle stream flowing downward and becoming a portion of the sidestream.

9. The process of claim 8 further characterized in that the feed aromatic hydrocarbon is benzene.

10. The process of claim 9 further characterized in that the reaction zone comprises a bed of a zeolitic alkylation catalyst.

11. The process of claim 9 further characterized in that the reaction zone comprises a bed of an SPA type catalyst.

12. The process of claim 8 further characterized in that a second portion of the recycle stream is passed into the rectification zone of the rectified separation zone.

13. The process of claim 12 further characterized in that the first portion of the recycle stream is heated by indirect heat exchange against the overhead vapor stream prior to passage into the contact-exchanging zone.

14. The process of claim 13 further characterized in that the product aromatic hydrocarbon is cumene.

* * * * *